(12) United States Patent
Kang et al.

(10) Patent No.: US 10,773,281 B2
(45) Date of Patent: Sep. 15, 2020

(54) ANHYDROUS SUBSTRATE CLEANING COMPOSITION, SUBSTRATE TREATING METHOD, AND SUBSTRATE TREATING APPARATUS

(71) Applicant: SEMES CO., LTD., Chungcheongnam-do (KR)

(72) Inventors: Ki-Moon Kang, Chungcheongnam-do (KR); Anton Koriakin, Chungcheongnam-do (KR); In Il Jung, Chungcheongnam-do (KR); Hae-Won Choi, Daejeon (KR)

(73) Assignee: SEMES CO., LTD., Chungcheongnam-do (KR)

(*) Notice: Subject to any disclaimer, the term of this patent is extended or adjusted under 35 U.S.C. 154(b) by 136 days.

(21) Appl. No.: 15/721,188

(22) Filed: Sep. 29, 2017

(65) Prior Publication Data
US 2018/0093306 A1    Apr. 5, 2018

(30) Foreign Application Priority Data

Sep. 30, 2016   (KR) .................. 10-2016-0126626

(51) Int. Cl.
| | | |
|---|---|---|
| *C11D 7/50* | (2006.01) | |
| *B08B 7/00* | (2006.01) | |
| *H01L 21/67* | (2006.01) | |
| *C11D 11/00* | (2006.01) | |

(Continued)

(52) U.S. Cl.
CPC .......... *B08B 7/0021* (2013.01); *C11D 7/5022* (2013.01); *C11D 11/0047* (2013.01); *H01L 21/31133* (2013.01); *H01L 21/6708* (2013.01); *H01L 21/6719* (2013.01); *H01L 21/67051* (2013.01); *H01L 21/67109* (2013.01); *C07C 31/02* (2013.01)

(58) Field of Classification Search
CPC .............................. C11D 7/50; C11D 11/0047
USPC ........................................................ 510/175
See application file for complete search history.

(56) References Cited

U.S. PATENT DOCUMENTS

| | | | | |
|---|---|---|---|---|
| 2005/0224459 A1* | 10/2005 | Kezuka | ................. | C09K 13/08 216/83 |
| 2008/0041823 A1* | 2/2008 | La | ......................... | C03C 15/00 216/97 |

(Continued)

FOREIGN PATENT DOCUMENTS

| | | |
|---|---|---|
| CN | 1563315 A | 1/2005 |
| CN | 101883688 A | 11/2010 |

(Continued)

OTHER PUBLICATIONS

Korean Examination Report dated Nov. 21, 2017, 14 pages.
Office Action for related CN App No. 201710899501.1 dated Jul. 23, 2019, 7 pgs.

*Primary Examiner* — Gregory E Webb
(74) *Attorney, Agent, or Firm* — Procopio, Cory, Hargreaves & Savitch LLP

(57) ABSTRACT

Disclosed are an anhydrous substrate cleaning composition, a substrate treating method, and a substrate treating apparatus. The substrate cleaning composite includes an etching compound that provides a component for treating a substrate, and a solvent that dissolves the etching compound, wherein the substrate cleaning composite is an anhydrous composite that does not include water.

15 Claims, 6 Drawing Sheets

(51) Int. Cl.
*H01L 21/311* (2006.01)
*C07C 31/02* (2006.01)

(56) References Cited

U.S. PATENT DOCUMENTS

| | | | | |
|---|---|---|---|---|
| 2009/0192065 A1* | 7/2009 | Korzenski | ............... | C11D 7/08 |
| | | | | 510/176 |
| 2010/0210068 A1* | 8/2010 | Lee | ................ | H01L 45/06 |
| | | | | 438/102 |
| 2015/0368099 A1* | 12/2015 | Kundalgurki | ....... | B81C 1/00849 |
| | | | | 438/50 |
| 2015/0368557 A1* | 12/2015 | Lee | ................ | H01L 21/76802 |
| | | | | 252/79.1 |

FOREIGN PATENT DOCUMENTS

| | | |
|---|---|---|
| CN | 103725455 A | 4/2014 |
| CN | 104488068 A | 4/2015 |
| CN | 105683336 A | 6/2016 |
| CN | 106547178 A | 3/2017 |
| JP | 2007-526653 A | 9/2007 |
| KR | 1020040027908 A | 4/2004 |
| KR | 1020040073584 A | 8/2004 |
| KR | 1020060015589 A | 2/2006 |
| KR | 1020070113096 A | 11/2007 |
| KR | 10-2007-0121309 A | 12/2007 |
| KR | 10-0835752 B1 | 6/2008 |
| KR | 10-2014-0017315 A | 2/2014 |

* cited by examiner

ANHYDROUS SUBSTRATE CLEANING COMPOSITION, SUBSTRATE TREATING METHOD, AND SUBSTRATE TREATING APPARATUS

CROSS-REFERENCE TO RELATED APPLICATIONS

A claim for priority under 35 U.S.C. § 119 is made to Korean Patent Application No. 10-2016-0126626 filed on Sep. 30, 2016, in the Korean Intellectual Property Office, the entire contents of which are hereby incorporated by reference.

BACKGROUND

Embodiments of the inventive concept described herein relate to an anhydrous substrate cleaning composition, a substrate treating method, and a substrate treating apparatus.

A semiconductor device is manufactured via various processes, such as a photolithography process of forming a circuit pattern on a substrate such as a silicon wafer. In a process of manufacturing a semiconductor device, various foreign substances such as particles, organic contaminants, metal impurities are produced. The foreign substances cause defects in the substrate, acting as a factor that directly influences the performance and yield rate of the semiconductor device. Accordingly, the process of manufacturing the semiconductor device is essentially accompanied by a cleaning process for removing the foreign substances.

The cleaning process performed via a chemical process of removing foreign substances on a substrate, a washing process of washing a chemical with pure water, and a drying process of drying the substrate. The general drying process has been performed in a method of substituting pure water on a substrate with an organic solvent, such as isopropyl alcohol (IPA), which has a relatively low surface tension, and evaporating it. Further, even though an organic solvent is used in the drying process, the semiconductor having a fine circuit pattern of a line width of 30 nm or less may undergo a pattern collapse.

SUMMARY

Embodiments of the inventive concept provide an anhydrous substrate cleaning composition that may efficiently treat a substrate, a substrate treating method, and a substrate treating apparatus.

Embodiments of the inventive concept also provide an anhydrous substrate cleaning composition having an improved cleaning efficiency, a substrate treating method, and a substrate treating apparatus.

Embodiments of the inventive concept also provide an anhydrous substrate cleaning composition that may prevent a pattern collapse, a substrate treating method, and a substrate treating apparatus.

The objects of the inventive concept are not limited to the above-described ones. Other technical objects that are not mentioned will be clearly understood from the following description by those skilled in the art to which the inventive concept pertains.

In accordance with an aspect of the inventive concept, there is provided a substrate cleaning composite including an etching compound that provides a component for treating a substrate, and a solvent that dissolves the etching compound, wherein the substrate cleaning composite is an anhydrous composite that does not include water.

The etching compound may include fluorine.

The etching compound may be ammonium fluoride.

The etching compound may be hydrogen fluoride.

The solvent may be acetic anhydride.

The solvent may be acetic acid.

The solvent may be propylene carbonate.

The substrate cleaning composite may further include a phase change assistant material that improves a solubility of a supercritical fluid.

The phase change assistant material may be alcohol.

The phase change assistant material may be isopropyl alcohol.

The phase change assistant material may be methanol.

The phase change assistant material may be ethanol.

The substrate cleaning composite may further include a binder that prevents particles separated from the substrate from being attached to the substrate again.

The binder may be isopropoxy ethanol.

In accordance with another aspect of the inventive concept, there is provided a substrate cleaning composite including an etching compound that provides a component for treating a substrate, a solvent that dissolves the etching compound, and a phase change assistant material that improves a solubility for a supercritical fluid.

The substrate cleaning composite may further include a binder that prevents particles separated from the substrate from being attached to the substrate again.

The etching compound may be ammonium fluoride, and the solvent may be acetic anhydride.

The phase change assistant material may be isopropyl alcohol.

The binder is isopropoxy ethanol.

In accordance with another aspect of the inventive concept, there is provided a substrate treating method including applying a substrate cleaning composite including an etching compound and a solvent to a substrate that is stopped, and cleaning the substrate by supplying a supercritical fluid to the substrate, wherein the substrate cleaning composite includes an etching compound that provides a component for treating a substrate, and a solvent that dissolves the etching compound, and wherein the substrate cleaning composite is an anhydrous composite that does not include water.

In accordance with another aspect of the inventive concept, there is provided a substrate treating method including cleaning a substrate by supplying a substrate cleaning composite including an etching compound and a solvent to a substrate that is being rotated, and drying the substrate by supplying a supercritical fluid to the substrate, wherein the substrate cleaning composite includes an etching compound that provides a component for treating a substrate, and a solvent that dissolves the etching compound, and wherein the substrate cleaning composite is an anhydrous composite that does not contain water.

In accordance with another aspect of the inventive concept, there is provided a substrate treating method including treating a substrate by mixing a substrate cleaning composite including an etching compound and a solvent with a supercritical fluid and supplying the mixture to the substrate, wherein the substrate cleaning composite includes an etching compound that provides a component for treating a substrate, and a solvent that dissolves the etching compound, and wherein the substrate cleaning composite is an anhydrous composite that does not contain water.

The etching compound may be ammonium fluoride.

The solvent may be anhydrous acetic acid.

The substrate cleaning composite may further include a phase change assistant material that improves a solubility for a supercritical fluid.

The substrate cleaning composite may further include a binder.

The supercritical fluid may be carbon dioxide ($CO_2$).

In accordance with another aspect of the inventive concept, there is provided a substrate treating apparatus including a chamber, a support unit located inside the chamber and configured to support a substrate, and a fluid supply unit configured to mix a substrate cleaning composite with a supercritical fluid and supply the mixture into the chamber, wherein the substrate cleaning composite includes an etching compound that provides a component for treating a substrate, and a solvent that dissolves the etching compound, and wherein the substrate cleaning composite is an anhydrous composite that does not contain water.

In accordance with another aspect of the inventive concept, there is provided a substrate treating apparatus including a first process chamber for applying a substrate cleaning composite to a substrate, and a second process chamber for supplying a supercritical fluid to the substrate carried in while the substrate cleaning composite resides on the substrate, wherein the substrate cleaning composite includes an etching compound that provides a component for treating a substrate, and a solvent that dissolves the etching compound, and wherein the substrate cleaning composite is an anhydrous composite that does not contain water.

The first process chamber may include a support member configured to support the substrate, and a controller configured to control the support member, and the controller may control the support member such that the substrate is rotated when the substrate cleaning composite is applied.

The first process chamber may include a support member configured to support the substrate, and a controller configured to control the support member, and the controller may control the support member such that the substrate is stopped when the substrate cleaning composite is applied.

The substrate cleaning composite may include a solvent that liquefy the substrate cleaning composite, and an etching compound that provides a component for treating the substrate.

The etching compound may be ammonium fluoride.

The solvent may be anhydrous acetic acid.

The substrate cleaning composite may further include a phase change assistant material that improves a solubility for a supercritical fluid.

The phase change assistant material may be alcohol.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Hereinafter, exemplary embodiments of the inventive concept will be described in more detail with reference to the accompanying drawings. The embodiments of the inventive concept may be modified in various forms, and the scope of the inventive concept should not be construed to be limited to the following embodiments. The embodiments of the inventive concept are provided to describe the inventive concept for those skilled in the art more completely. Accordingly, the shapes of the components of the drawings are exaggerated to emphasize clearer description thereof.

Hereinafter, a substrate treating apparatus 100 according to the inventive concept will be described.

The substrate treating apparatus 100 may perform a supercritical process of processing a substrate S by using a supercritical fluid as a process fluid.

Here, the substrate S is an inclusive concept including a semiconductor device or a flat panel display (FPD), and other substrates used for manufacturing objects in which a circuit pattern is formed on a thin film. Examples of such substrates S include silicon wafers, glass substrates, and organic substrates.

Figure 1:
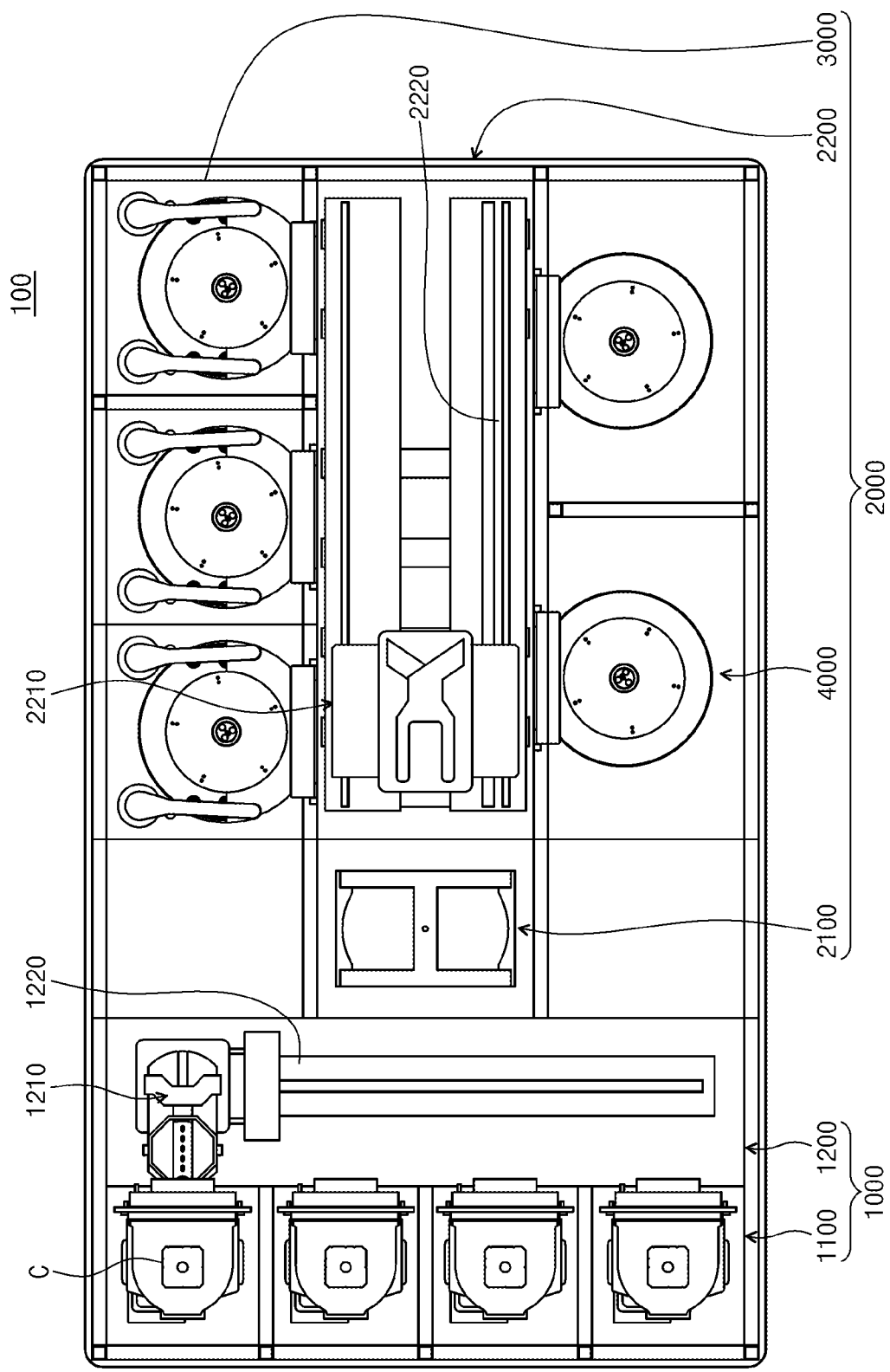
FIG. 1 is a plan view illustrating a substrate treating apparatus according to an embodiment of the inventive concept.

FIG. 1 is a plan view illustrating a substrate treating apparatus according to an embodiment of the inventive concept.

Referring to FIG. 1, the substrate treating apparatus 100 includes an index module 1000 and a process module 2000.

The index module 1000 receives a substrate S from the outside and transfers the substrate S to the process module 2000. The process module 2000 may perform a supercritical drying process.

The index module 1000 is an equipment front end module (EFEM), and includes a load port 1100 and a feeding frame 1200.

A container C in which the substrate S is accommodated is positioned on the load port 1100. A front opening unified pod (FOUP) may be used as the container C. The container C may be carried into the load port 1100 from the outside by an overhead transfer, or may be carried out of the load port 1100.

The feeding frame 1200 transfers the substrate S between the container C positioned on the load port 1100 and the process module 2000. The feeding frame 1200 includes an index robot 1210 and an index rail 1220. The index robot 1210 may transfer the substrate S while moving on the index rail 1220.

The process module 2000 includes a buffer chamber 2100, a feeding chamber 2200, a first process chamber 3000, and a second process chamber 4000.

The buffer chamber 2100 provides a space in which the substrate S transferred between the index module 1000 and the process module 2000 temporarily stays. A buffer slot may be provided in the buffer chamber 2100. The substrate S is positioned in the buffer slot. For example, the index robot 1210 may extract the substrate S from the container C and may position the substrate S in the buffer slot. The feeding robot 2210 of the feeding chamber 2200 may extract the substrate S positioned in the buffer slot, and may transfer the substrate S to the first process chamber 3000 or the second process chamber 4000. A plurality of buffer slots may be provided in the buffer chamber 2100, and a plurality of substrates S may be positioned in the buffer slots.

The feeding chamber 2200 transfers the substrate S between the buffer chamber 2100 disposed at a circumference of the feeding chamber 2200, the first process chamber 3000, and the second process chamber 4000. The feeding chamber 2200 may include a feeding robot 2210 and a feeding rail 2220. The feeding robot 2210 may transfer the substrate S while moving on the feeding rail 2220.

The first process chamber 3000 and the second process chamber 4000 may perform a cleaning process. Then, the cleaning process may be sequentially performed by the first process chamber 3000 and the second process chamber 4000. For example, the first process chamber 3000 may perform a cleaning process, and subsequently, the second process chamber 4000 may perform a supercritical drying process. Further, the second process chamber 4000 may perform a cleaning process and a drying process.

The first process chamber 3000 and the second process chamber 4000 are disposed on side surfaces of the feeding chamber 2200. For example, the first process chamber 3000 and the second process chamber 4000 are disposed on different side surface of the feeding chamber 2200 to face each other.

The process module 2000 may include a plurality of first process chambers 3000 and a plurality of second process chambers 4000. The plurality of process chambers 3000 and 4000 may be disposed in a row on a side surface of the feeding chamber 2200, may be disposed to be stacked on one another, or may be disposed through a combination thereof.

Of course, the disposition of the first process chamber 3000 and the second process chamber 4000 is not limited to the aforementioned example, and may be changed in consideration of a footprint or a process efficiency of the substrate treating apparatus 100. The substrate treating apparatus 100 may be controlled by a controller 5000 (see FIG. 2).

Figure 2:
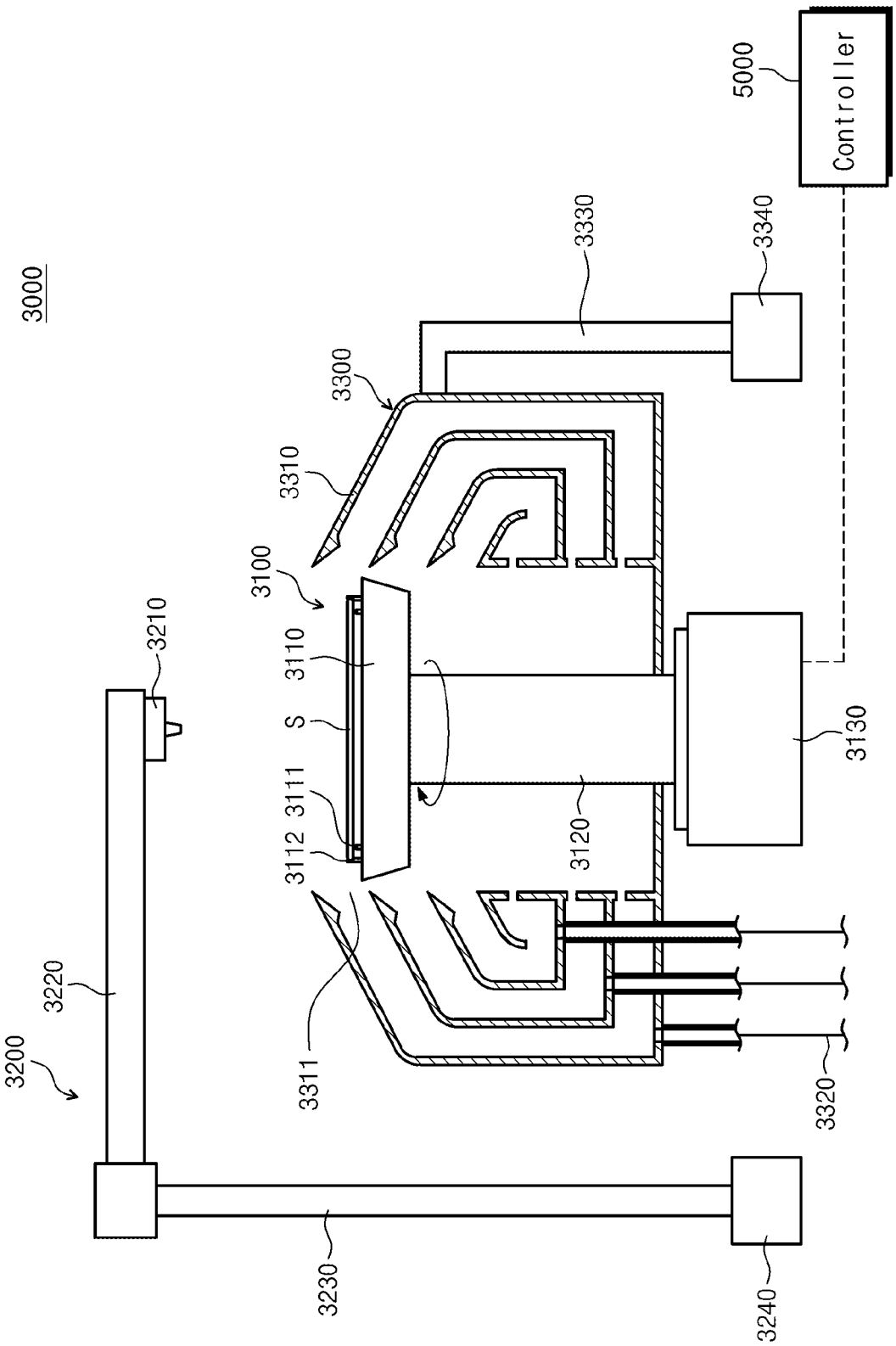
FIG. 2 is a sectional view of a first process chamber of FIG. 1.

FIG. 2 is a sectional view of a first process chamber of FIG. 1.

Referring to FIG. 2, the first process chamber 3000 includes a support member 3100, a nozzle member 3200, and a recovery member 3300.

The first process chamber 3000 may clean the substrate through an anhydrous substrate cleaning composition. The process performed in the first process chamber 3000 is performed by an anhydrous process that does not use water.

The support member 3100 supports the substrate S. The support member 3100 may rotate the supported substrate S. The support member 3100 includes a support plate 3110, a support pin 3111, a chuck pin 3112, a rotary shaft 3120, and a rotation driver 3130.

The support plate 3110 has an upper surface having a shape that is the same as or similar to the substrate S. A support pin 3111 and a chuck pin 3112 are formed on the upper surface of the support plate 3110. The support pin 3111 supports a bottom surface the substrate S. The chuck pin 3112 may fix the supported substrate S.

A rotary shaft 3120 is connected to a lower portion of the support plate 3110. The rotary shaft 3120 receives a rotational force from the rotation driver 3130 and rotates the support plate 3110. Accordingly, the substrate S positioned on the support plate 3110 may be rotated. The chuck pin 3112 prevents the substrate S from deviating from a proper location.

The nozzle member 3200 ejects an anhydrous substrate cleaning composition to the substrate S. The nozzle member 3200 includes a nozzle 3210, a nozzle bar 3220, a nozzle shaft 3230, and a nozzle shaft driver 3240.

The nozzle 3210 ejects the anhydrous substrate cleaning composition to the substrate S positioned on the support plate 3110. The nozzle 3210 is formed on the bottom surface of one end of the nozzle bar 3220. The nozzle bar 3220 is coupled to a nozzle shaft 3230. The nozzle shaft 3230 is provided to elevate or rotate. The nozzle shaft driver 3240 may adjust the location of the nozzle 3210 by elevating or rotating the nozzle shaft 3230.

The recovery member 3300 recovers the anhydrous substrate cleaning composition supplied to the substrate S. If the anhydrous substrate cleaning composition is supplied to the substrate S by the nozzle member 3200, the support member 3100 may uniformly supply the anhydrous substrate cleaning composition to the entire area of the substrate S by rotating the substrate S. If the substrate S is rotated, the anhydrous substrate cleaning composition spatters from the substrate S. The spattering anhydrous substrate cleaning composition may be recovered by the recovery member 3300.

The recovery member 3300 may include a recovery vessel 3310, a recovery line 3320, an elevation bar 3330, and an elevation driver 3340.

The recovery vessel 3310 is provided to have an annular ring shape that surrounds the support plate 3110. A plurality of recovery vessels 3310 may be provided. The plurality of recovery vessels 3310 have a ring shape and sequentially become far away from the support plate 3110 when viewed from the top. The recovery vessels 3310 have larger heights as they go far away from the support plate 3110. A recovery hole 3311, through which the anhydrous substrate cleaning composition spattering from the substrate S is introduced, is formed in a space between the recovery vessels 3310.

A recovery line 3320 is formed on the lower surface of the recovery vessel 3310.

The elevation bar 3330 is connected to the recovery vessel 3310. The elevation bar 3330 receives power from the elevation driver 3340 and moves the recovery vessel 3310 upwards and downwards. When a plurality of recovery vessels 3310 are provided, the elevation bar 3330 may be connected to the outermost recovery vessel 3310. The elevation driver 3340 may adjust a recover hole 3311, through which the spattering anhydrous substrate cleaning composition is introduced, from a plurality of recovery holes 3311 by elevating the recovery vessels 3310 through the elevation bar 3330.

The anhydrous cleaning composition according to the embodiment of the inventive concept is an anhydrous composition including fluorine. The anhydrous substrate cleaning composition includes an etching compound, a solvent, and a phase change assistant material.

One of the conventional chemicals used for cleaning a substrate is SC-1 (a mixture of ammonia and hydrogen peroxide). SC-1 is effective for removing particles residing on a surface of a substrate after treatment of the substrate. However, the cleaning of the substrate through SC-1 cannot be applied when a hydrophobic film is cleaned or a metal is present on a surface of the substrate. Further, the characteristics, by which ammonia is evaporated from the ammonia peroxide, makes it difficult to manage a concentration of ammonia peroxide. Further, because SC-1 contains water, a pattern collapse may be caused in a drying process.

Another example of the conventional chemicals used for cleaning a substrate is diluted hydrogen fluoride (DHF). DHF is effective for removing a silicon dioxide layer from a surface of a substrate after treatment of the substrate. However, hydrogen fluoride is dangerous when it is used because it is very harmful to the human body, and the concentration of hydrogen fluoride easily changes in DHF. Further, because DHF also contains water, a pattern collapse may be caused in a drying process.

The anhydrous substrate cleaning composition according to the inventive concept is provided instead of the conventional chemical not to include water.

The etching compound provides fluoride that contributes to treatment of a substrate. The etching compound may be ammonium fluoride ($NH_4F$) Ammonium fluoride is salt of hydrofluoric acid and ammonia, is provided in the form of crystal, and provides ammonium and fluorine. Accordingly, the anhydrous substrate treating composite may be used for cleaning a substrate using conventional SC-1 and DHF. Further, ammonium fluoride is provided in the form of salt, and accordingly, because an amount of ammonium fluoride contained in the anhydrous substrate cleaning composite and a timing at which ammonium fluoride is mixed may be adjusted, concentration may be adjusted. Further, because ammonium fluoride does not contain hydrogen fluoride, the harmfulness to the body is reduced.

The solvent is provided such that the anhydrous substrate cleaning composite is in a liquid state or is similar to a liquid. Ammonium fluoride, which is an etching compound, is provided in the form of crystal. When ammonium fluoride is in the state of crystal, substrate cleaning efficiency may be reduced. Accordingly, the cleaning efficiency may be improved by dissolving ammonium fluoride through the solvent. The solvent may include acetic anhydride $(CH_3O)_2O)$, acetic acid, and propylene carbonate.

The phase change assistant material makes the anhydrous substrate cleaning composite affinitive to the supercritical fluid. That is, the phase change assistant material allows the anhydrous substrate cleaning composite to be effectively dissolved in the supercritical fluid if the anhydrous substrate cleaning composite meets the supercritical fluid. The phase change assistant material is alcohol. As an example, the organic solvent may include isopropyl alcohol, methanol, and ethanol. The conventional chemical, such as SC-1 or DHF, include water as a composition. The pattern formed in the substrate gradually becomes finer, and the line width of the pattern gradually becomes smaller. The water has a surface tension so that the penetration force into narrow spaces between the patterns is low, and accordingly, the cleaning efficiency for the spaces between the patterns is low. Further, in the cleaning using the conventional chemical, such as SC-1 or DHF, a drying process is performed after the chemical is substituted by deionized water, and pattern leaning or pattern collapsing may occur even in the drying process. Meanwhile, the anhydrous substrate cleaning composite according to the inventive concept does not contain water, and accordingly, the conventional problem caused by the water contained in the chemical does not occur.

The anhydrous substrate cleaning composite may include ammonium fluoride, a phase change assistant material, and a solvent at the following ratio.

TABLE 1

| Composition | wt % |
| --- | --- |
| Ammonium fluoride | 0.22~5.5 |
| Phase change assistant material | 83.5~95 |
| Solvent | 1.1~11 |

Figure 3:
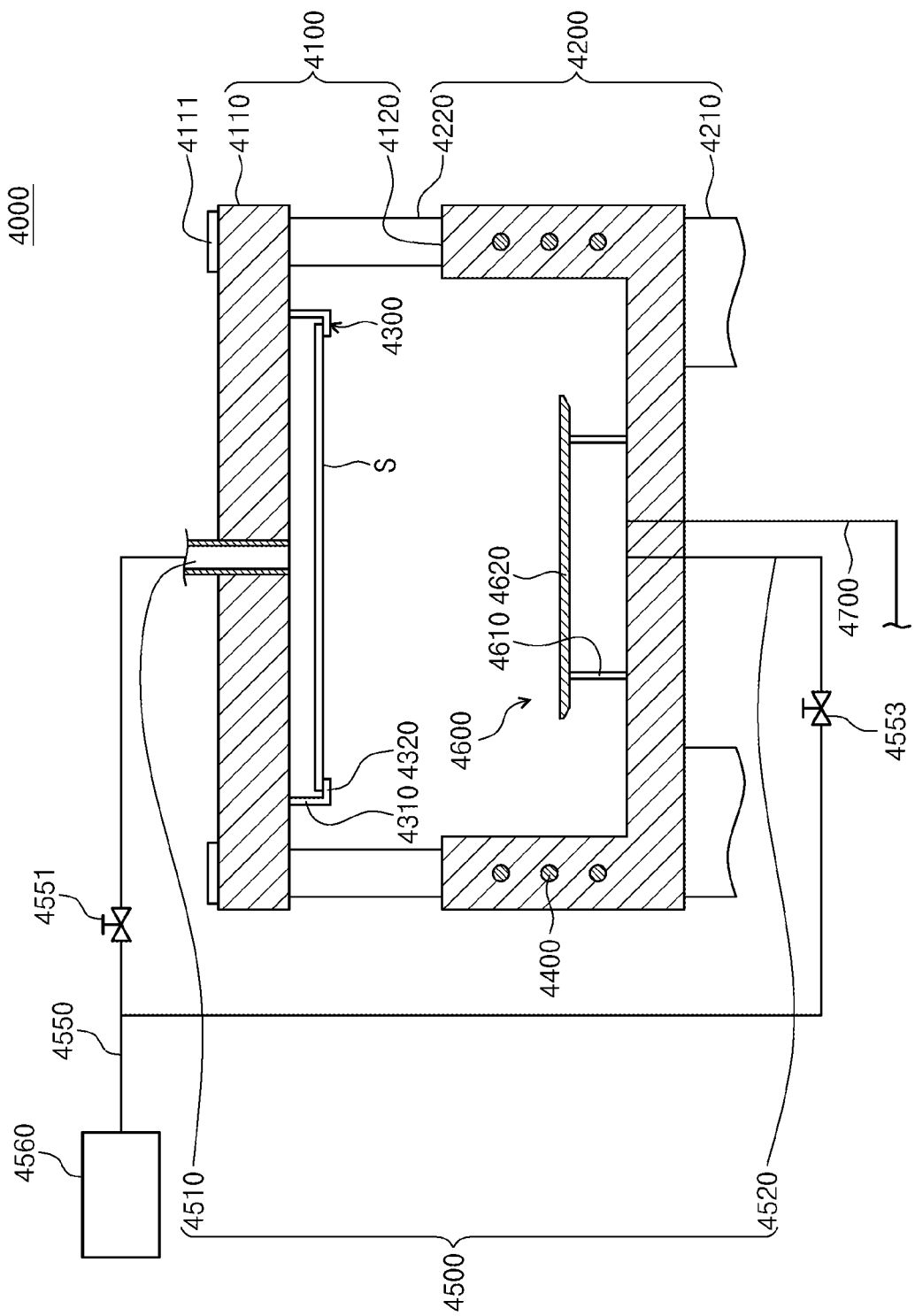
FIG. 3 is a sectional view of an embodiment of the second process chamber of FIG. 1.

FIG. 3 is a sectional view of an embodiment of the second process chamber of FIG. 1.

Referring to FIG. 3, the second process chamber 4000 may include a chamber 4100, an elevation member 4200, a support unit 4300, a heating member 4400, a fluid supply unit 4500, a blocking member 4600, an exhaust member 4700, and an agitation unit 4800. The second process chamber 4000 performs a process of treating a substrate by using a supercritical fluid.

The chamber 4100 provides a treatment space in which a supercritical drying process is performed, in the interior thereof. The chamber 4100 is formed of a material that endures a high pressure of more than a critical pressure.

The chamber 4100 includes an upper body 4110 and a lower body 4120. The lower body 4120 is coupled to the upper body 4110 under the upper body 4110. The space generated through combination of the upper body 4110 and the lower body 4120 is provided as a treatment space for performing a substrate treating process.

The upper body 4110 is fixedly installed in an external structure. The lower body 4120 is provided to be elevated with respect to the upper body 4110. If the lower body 4120 is lowered to be spaced apart from the upper body 4110, the treatment space is opened to the interior of the second process chamber 4000. Through the opened treatment space, the substrate S may be carried into or carried out of the interior space of the second process chamber 4000. Here, the substrate S carried into the second process chamber 4000 may be in a state in which the anhydrous substrate cleaning composite applied in the first process chamber 3000 resides. If the lower body 4120 is lifted to be attached to the upper body 4110, the treatment space is closed from the interior of the second process chamber 4000. In the closed treatment space, the substrate may be treated through the supercritical fluid. Unlike the above-described example, the lower body 4120 may be fixedly installed in the chamber 4100, and the upper body 4110 may be elevated.

The elevation unit 4220 elevates the lower body 4120. The elevation unit 4200 includes an elevation cylinder 4210 and an elevation rod 4220. The elevation cylinder 4210 is coupled to the lower body 4120 to generate a vertical driving force. While the substrate is treated by using the supercritical fluid, the elevation cylinder 4210 generates a driving force that is high enough to seal the second process chamber 400 by overcoming a high pressure of a threshold pressure or more in the interior of the second process chamber 4000 and attaching the upper body 4110 and the lower body 4120. One end of the elevation rod 4220 is inserted into the elevation cylinder 4210 and extends vertically upwards, and an opposite end of the elevation rod 4220 is coupled to the upper body 4110. If a driving force is generated in the elevation cylinder 4210, the elevation cylinder 4210 and the elevation rod 4220 may be relatively elevated, and the lower body 4120 coupled to the elevation cylinder 4210 also may be elevated. When the lower body 4120 is elevated by the elevation cylinder 4210, the elevation rod 4220 may prevent the upper body 4110 and the lower body 4120 from moving horizontally and guide the elevation direction of the lower body 4120, thereby preventing the upper body 4110 and the lower body 4120 from deviating from a proper location.

The support unit 4300 is located in the treatment space of the chamber 4100 to support the substrate S. The support unit 4300 is coupled to the upper body 4110. The support unit 4300 includes a vertical part 4320 and a horizontal part 4310.

The vertical part 4320 extends downwards from an upper wall of the chamber 4100. The vertical part 4320 is installed on a lower surface of the upper body 4110. The vertical part 4320 extends to the lower side of the upper body 4110. An end of the vertical part 4320 is coupled to the horizontal part 4310 perpendicularly to the horizontal part 4310. The horizontal part 4310 extends from an end of the vertical part 4320 to an inside of the chamber 4100. The substrate S is positioned on the horizontal part 4310. The horizontal part 4310 supports a bottom surface of a peripheral area of the substrate S.

The support unit 4300 may contact a peripheral area of the substrate S to support the substrate S so that treatment of the substrate S through the supercritical fluid may be performed on an entire area of the upper surface of the substrate S and almost all area of the lower surface of the substrate S. Here, the upper surface of the substrate S may be a pattern surface, and the lower surface of the substrate S may be a non-pattern surface.

The support unit 4300 is installed in the upper body 4110. The support unit 4300 may support the substrate S relatively stably while the lower body 4120 is elevated.

A horizontality adjusting member 4111 is installed in the upper body 4110, in which the support unit 4300 is installed. The horizontality adjusting member 4111 adjusts a horizontality of the upper body 4110. The horizontality of the substrate S positioned on the support unit 4300 installed in the upper body 4110 is adjusted by adjusting the horizontality of the upper body 4110. The upper body 4110 is elevated and the lower body 4120 is fixed, and when the upper unit 4300 is installed in the lower body 4120, the horizontality adjusting member 4111 may be installed in the lower body 4120.

The heating member 4400 heats the interior of the second process chamber 4000. The heating member 4400 heats the supercritical fluid supplied to the second process chamber 4000 to a critical temperature or higher to maintain a phase of the supercritical fluid. When the supercritical fluid is liquefied, the heating member 4400 may heat the supercritical fluid such that the liquefied supercritical fluid is converted into a supercritical fluid again. The heating member 4440 is buried in at least one wall of the upper body 4110 and the lower body 4120. The heating member 4440 receives electric power from the outside to generate heat. As an example, the heating member 4400 may be a heater.

The fluid supply unit 4500 supplies a fluid to the second process chamber 4000. The supplied fluid may be a supercritical fluid. As an example, the supplied supercritical fluid may be carbon dioxide. Further, the fluid supply unit 4500 may mix the supercritical fluid and the anhydrous substrate cleaning composite to supply the mixture.

The fluid supply unit 4500 includes an upper fluid supply unit 4510, a lower fluid supply unit 4520, a supply line 4550, and valves 4551 and 4553.

The upper fluid supply unit 4510 directly supplies the supercritical fluid to an upper surface of the substrate S. The upper fluid supply unit 4510 is connected to the upper body 4110. The upper fluid supply unit 4510 is connected to the upper body 4110 that faces a central upper surface of the substrate S.

The lower fluid supply unit 4520 supplies the supercritical fluid to a lower surface of the substrate S. The lower fluid supply unit 4520 is connected to the lower body 4120. The lower fluid supply unit 4520 is connected to the lower body 4120 that faces a central lower surface of the substrate S.

The supercritical fluid ejected from the upper fluid supply unit 4510 and the lower fluid supply unit 4520 reaches a central area of the substrate S and is uniformly provided to the whole area of the substrate S while being spread out to a peripheral area of the substrate S.

The supply line 4550 is connected to the upper fluid supply unit 4510 and the lower fluid supply unit 4520. The supply line receives the supercritical fluid from a supercritical fluid storage unit and supplies the supercritical fluid to the upper fluid supply unit 4510 and the lower fluid supply unit 4520.

The valves 4551 and 4553 are installed in the supply line 4550. A plurality of valves 4551 and 4553 may be provided in the supply line. The valves 4551 and 4553 adjust the flow rates of the supercritical fluid supplied to the upper fluid supply unit 4510 and the lower fluid supply unit 4520. The valves 4551 and 4553 may adjust the flow rate of the supercritical fluid supplied into the chamber 4110 by using a controller 5000.

First, in the fluid supply unit 4500, the lower fluid supply unit 4520 may supply the supercritical fluid. Thereafter, the upper fluid supply unit 4510 may supply the supercritical fluid. The supercritical drying process may be performed while the interior of the second process chamber 4000 does not reach a threshold pressure in an initial stage. When the interior of the second process chamber 4000 does not reach the threshold pressure, the supercritical fluid supplied into the interior of the second process chamber 4000 may be liquefied. If the supercritical fluid is liquefied, it drops to the substrate S due to the gravitational force, damaging the substrate S.

Accordingly, the lower fluid supply unit 4520 supplies the supercritical fluid first. After the supercritical fluid is supplied to the second process chamber 4000, the internal pressure of the second process chamber 4000 reaches the threshold pressure. After the internal pressure of the second process chamber 4000 reaches the threshold pressure, the upper fluid supply unit 4510 supplies the supercritical fluid. The lower fluid supply unit 4520 supplies the supercritical fluid earlier than the upper fluid supply unit 4510, thereby preventing the supercritical fluid from being liquefied and dropping to the substrate S.

The blocking member 4600 prevents the supercritical fluid supplied from the fluid supply unit 4500 from being directly ejected to a lower surface of the substrate S. The blocking member 4600 may include a blocking plate 4610 and a support 4620.

The blocking plate 4610 is located in the treatment space in the interior of the chamber 4100. The blocking plate 4610 is disposed between the support unit 4300 and the lower fluid supply unit 4520. The blocking plate 4610 have a shape corresponding to the substrate S. As an example, the blocking plate 4610 may have a circular plate shape. The radius of the blocking plate 4610 may be similar to or larger than that of the substrate S. The blocking plate 4610 may be located on a lower surface of the substrate S positioned on the support unit 4300 to prevent the supercritical fluid supplied through the lower fluid supply unit 4520 from being directly ejected to the lower surface of the substrate S. When the radius of the blocking plate 4610 is similar to or larger than that of the substrate S, the supercritical fluid may be perfectly interrupted from being directly ejected to the substrate S.

Alternatively, the radius of the blocking plate 4610 may be smaller than that of the substrate S. In this case, the supercritical fluid is interrupted from being directly ejected to the substrate S. Further, the supercritical fluid may be made to reach the substrate S relatively easily by minimally lowering the velocity of the supercritical fluid. When the radius of the blocking plate 4610 is smaller than that of the substrate S, a supercritical drying process for the substrate S may be effectively performed.

The support 4620 supports the blocking plate 4610. The support 4620 supports a rear surface of the blocking plate 4610. The support 4620 is installed on a lower wall of the chamber 4100 to be vertically installed. The blocking plate 4610 may be positioned on the support 4620 by the gravitational force of the block plate 4610 without any coupling.

Unlike this, the support 4620 and the blocking plate 4610 may be coupled to each other by using nuts and bolts. Further, the support 4620 and the blocking plate 4610 may be integrally formed.

The exhaust member 4700 exhausts the supercritical fluid from the second process chamber 4000. The exhaust member 4700 may be connected to the exhaust line 4750 that exhausts the supercritical fluid. Then, a valve (not illustrated) for adjusting the flow rate of the supercritical fluid exhausted to the exhaust line 4750 may be installed in the exhaust member 4700 The supercritical fluid exhausted through the exhaust line 4750 may be discharged to the air or may be supplied to a supercritical fluid recycling system (not illustrated). The exhaust member 4700 may be coupled to the lower body 4120.

At an late stage of the substrate treating process using the supercritical fluid, the supercritical fluid may be exhausted from the second process chamber 4000 so that the internal pressure of the second process chamber 4000 may be reduced to a critical pressure or lower and the supercritical fluid may be liquefied. The liquefied supercritical fluid may be discharged by the gravitational force through the exhaust member 4700 formed in the lower body 4120.

Figure 4:
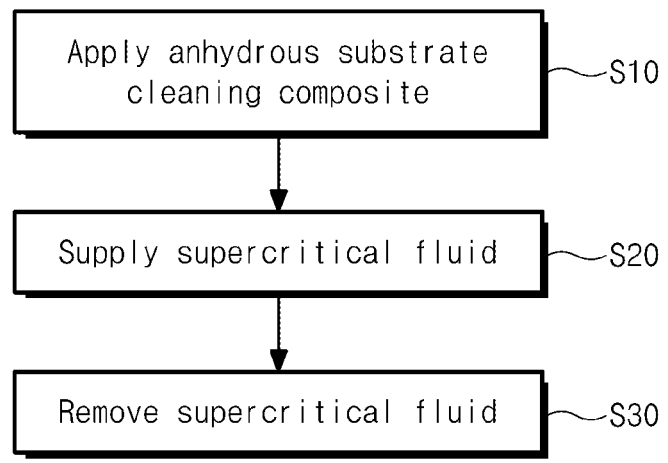
FIG. 4 is a view illustrating an operation of treating a substrate by using an anhydrous substrate cleaning composition according to the inventive concept.

FIG. 4 is a view illustrating an operation of treating a substrate by using an anhydrous substrate cleaning composition according to the inventive concept.

Referring to FIG. 4, a preset amount of the anhydrous substrate cleaning composite is applied to an upper surface of the substrate (S10). The anhydrous substrate cleaning composite may be applied in the first process chamber 3000. Then, the support member 3100 may be stopped. Thereafter, the substrate S carried into the second process chamber 4000 while the anhydrous substrate cleaning composite resides on the upper surface of the substrate S, and the supercritical fluid is supplied to the substrate S (S20). The supercritical fluid may be a carbon dioxide supercritical fluid.

If the anhydrous substrate cleaning composite meets the supercritical fluid, it is dissolved in the supercritical fluid. If the phase change assistant material is alcohol, the anhydrous substrate cleaning composite may improve a degree by which the supercritical fluid is dissolved. If the anhydrous substrate cleaning composite is provided to a periphery of the upper surface of the substrate while being dissolved in the supercritical fluid, the penetration force of the anhydrous substrate cleaning composite into a narrow space increases. Accordingly, the cleaning of the substrate is effectively performed on the pattern formed in the substrate as well as a surface of the substrate.

If a preset time elapses, the supercritical fluid in which the anhydrous substrate cleaning composite is dissolved is removed around the substrate (S30). Then, the particles and the anhydrous substrate cleaning composite are removed together with the supercritical fluid around the substrate S.

Figure 5:
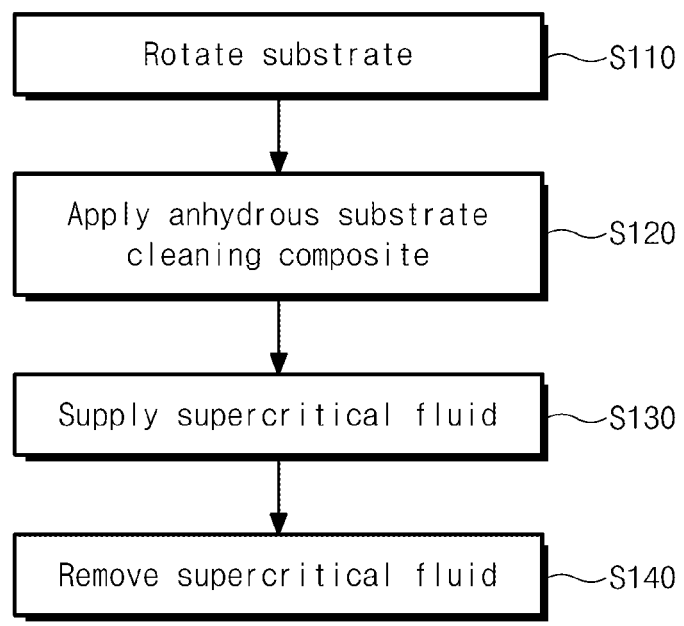
FIG. 5 is a view illustrating an operation of treating a substrate by using an anhydrous substrate cleaning composition according to another embodiment.

FIG. 5 is a view illustrating an operation of treating a substrate by using an anhydrous substrate cleaning composition according to another embodiment.

Referring to FIG. 5, the substrate S supported by the support member 3100 may be provided while being rotated (S110). Further, the anhydrous substrate cleaning composite is applied to the upper surface of the substrate S (S120). Although FIG. 5 illustrates that the rotation of the substrate S is initiated prior to the application of the anhydrous substrate cleaning composite, the rotation of the substrate S may be initiated together with the supply of the anhydrous substrate cleaning composite or may be initiated after the anhydrous substrate cleaning composite is supplied. The anhydrous substrate cleaning composite may be applied in the first process chamber 3000.

Figure 6:
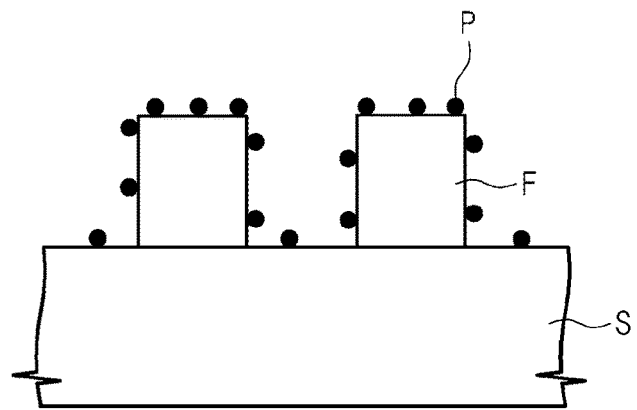
FIG. 6 is a view illustrating a state of a substrate before an anhydrous substrate cleaning composition is supplied.
Figure 7:
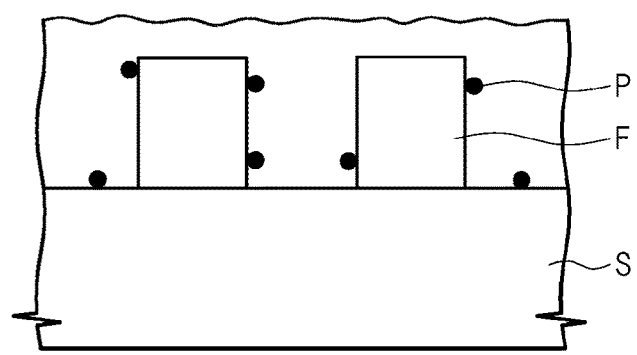
FIG. 7 is a view illustrating a state of a substrate an anhydrous substrate cleaning composition is supplied
Figure 8:
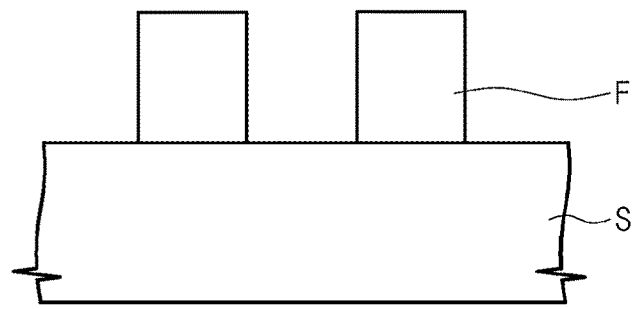
FIG. 8 is a view illustrating a substrate in a state in which treatment is made by an anhydrous substrate cleaning composition.

FIG. 6 is a view illustrating a state of a substrate before an anhydrous substrate cleaning composition is supplied. FIG. 7 is a view illustrating a state of a substrate an anhydrous substrate cleaning composition is supplied. FIG. 8 is a view illustrating a substrate in a state in which treatment is made by an anhydrous substrate cleaning composition.

Referring to FIG. 6, the rotating substrate S may be cleaned by the anhydrous substrate cleaning composite. As the substrate S is rotated, the anhydrous substrate cleaning composite containing particles spatters to the outside. The anhydrous substrate cleaning composite continues to be supplied to the substrate for a preset time period, and the anhydrous substrate cleaning composite may reside on the upper surface of the substrate S.

FIG. 8 is a view illustrating a substrate in a state in which the treatment of the substrate is completed through the supercritical fluid.

The substrate S treated by the anhydrous substrate cleaning composite while being rotated is carried into the second process chamber 4000 while the anhydrous substrate cleaning composite resides on the upper surface of the substrate S, and the supercritical fluid is supplied to the substrate S (S130). Accordingly, similarly to the treatment of the substrate of FIG. 4, the anhydrous substrate cleaning composite is dissolved in the supercritical fluid if it meets the supercritical fluid. Further, in the process, the particles P residing in the substrate S may be removed from the substrate S. If a preset time elapses, the supercritical fluid in which the anhydrous substrate cleaning composite is dissolved is removed around the substrate (S140).

Figure 9:
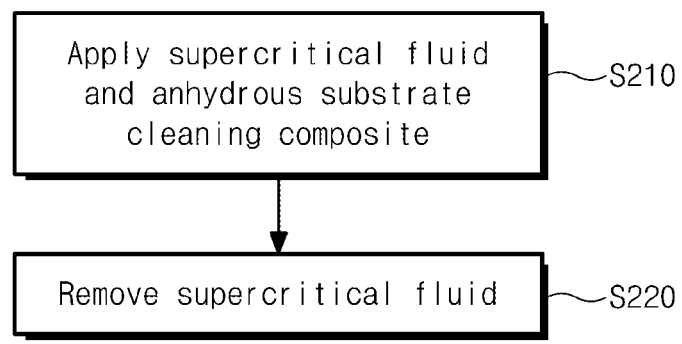
FIG. 9 is a view illustrating an operation of treating a substrate by using an anhydrous substrate cleaning composition according to another embodiment.

FIG. 9 is a view illustrating an operation of treating a substrate by using an anhydrous substrate cleaning composition according to another embodiment.

The anhydrous substrate cleaning composite according to the inventive concept may be supplied to the substrate S in the second process chamber 4000. As an example, the anhydrous substrate cleaning composite may be supplied to the substrate after being mixed with the supercritical gas (S210). In detail, the anhydrous substrate cleaning composite may be supplied to a periphery of the substrate after being mixed with the supercritical gas. The anhydrous substrate cleaning composite contained in the supercritical fluid reacts with the substrate S to remove particles from the substrate S.

Further, if a preset time elapses and the substrate S is cleaned, the supercritical fluid may be removed around the substrate S (S220).

The anhydrous substrate cleaning composite according to the inventive concept may further include a binder. The binder is located on outer surfaces of particles if it meets the particles to form micelles. In the process of cleaning the substrate, the particles separated from the substrate are attached to the substrate again, resulting in reduction of the cleaning efficiency. Meanwhile, if the binder is located on the outer surfaces of the particles to form micelles, the particles may be interrupted from contacting the substrate and may be prevented from being attached to the substrate again. The binder may be isopropoxy ethanol.

The anhydrous substrate cleaning composite may include ammonium fluoride, a phase change assistant material, a solvent, and a binder at the following ratio.

TABLE 2

| Composition | wt % |
|---|---|
| Ammonium fluoride | 0.2~5 |
| Phase change assistant material | 75~95 |
| Solvent | 1~10 |
| Binder | 0.1~10 |

The anhydrous substrate cleaning composite according to the inventive concept may further include hydrogen fluoride. Then, hydrogen fluoride may be contained in the anhydrous substrate cleaning composite together with ammonium fluoride ($NH_4F$) or instead of ammonium fluoride ($NH_4F$).

According to an embodiment of the inventive concept, an anhydrous substrate cleaning composite that efficiently treats a substrate, a substrate treating apparatus and a substrate treating method may be provided.

According to an embodiment of the inventive concept, an anhydrous substrate cleaning composite having an improved cleaning efficiency, a substrate treating apparatus and a substrate treating method may be provided.

According to an embodiment of the inventive concept, an anhydrous substrate cleaning composite that prevents a pattern collapse, a substrate treating apparatus and a substrate treating method may be provided.

The above description exemplifies the inventive concept. Furthermore, the above-mentioned contents describe the exemplary embodiment of the inventive concept, and the inventive concept may be used in various other combinations, changes, and environments. That is, the inventive concept can be modified and corrected without departing from the scope of the inventive concept that is disclosed in the specification, the equivalent scope to the written disclosures, and/or the technical or knowledge range of those skilled in the art. The written embodiment describes the best state for implementing the technical spirit of the inventive concept, and various changes required in the detailed application fields and purposes of the inventive concept can be made. Accordingly, the detailed description of the inventive concept is not intended to restrict the inventive concept in the disclosed embodiment state. Furthermore, it should be construed that the attached claims include other embodiments.

What is claimed is:

1. A substrate cleaning composite comprising:
   an etching compound that provides a component for treating a substrate;
   a binder that prevents particles separated from the substrate from being attached to the substrate again, wherein the binder is isopropoxy ethanol; and
   a solvent that dissolves the etching compound,
   wherein the substrate cleaning composite is an anhydrous composite that does not include water.

2. The substrate cleaning composite of claim 1, wherein the etching compound includes fluorine.

3. The substrate cleaning composite of claim 1, wherein the etching compound is ammonium fluoride.

4. The substrate cleaning composite of claim 1, wherein the etching compound is hydrogen fluoride.

5. The substrate cleaning composite of claim 1, wherein the solvent is acetic anhydride.

6. The substrate cleaning composite of claim 1, wherein the solvent is acetic acid.

7. The substrate cleaning composite of claim 1, wherein the solvent is propylene carbonate.

8. The substrate cleaning composite of claim 1, further comprising:
   a phase change assistant material that improves a solubility of a supercritical fluid.

9. The substrate cleaning composite of claim 8, wherein the phase change assistant material is alcohol.

10. The substrate cleaning composite of claim 8, wherein the phase change assistant material is isopropyl alcohol.

11. The substrate cleaning composite of claim 8, wherein the phase change assistant material is methanol.

12. The substrate cleaning composite of claim 8, wherein the phase change assistant material is ethanol.

13. A substrate cleaning composite comprising:
    an etching compound that provides a component for treating a substrate;
    a binder that prevents particles separated from the substrate from being attached to the substrate again, wherein the binder is isopropoxy ethanol;
    a solvent that dissolves the etching compound; and
    a phase change assistant material that improves a solubility for a supercritical fluid.

14. The substrate cleaning composite of claim 13, wherein the etching compound is ammonium fluoride, and
    wherein the solvent is acetic anhydride.

15. The substrate cleaning composite of claim 14, wherein the phase change assistant material is isopropyl alcohol.

* * * * *